(12) United States Patent
Ma

(10) Patent No.: US 12,129,420 B2
(45) Date of Patent: *Oct. 29, 2024

(54) EMULSIFIERS

(71) Applicant: Bunge Loders Croklaan B.V., Wormerveer (NL)

(72) Inventor: Jun Ma, Wormerveer (NL)

(73) Assignee: BUNGE LODERS CROKLAAN B.V., Wormerveer (NL)

( * ) Notice: Subject to any disclaimer, the term of this patent is extended or adjusted under 35 U.S.C. 154(b) by 497 days.

This patent is subject to a terminal disclaimer.

(21) Appl. No.: 16/499,596

(22) PCT Filed: May 4, 2018

(86) PCT No.: PCT/EP2018/061613
§ 371 (c)(1),
(2) Date: Sep. 30, 2019

(87) PCT Pub. No.: WO2018/206464
PCT Pub. Date: Nov. 15, 2018

(65) Prior Publication Data
US 2021/0106961 A1    Apr. 15, 2021

(30) Foreign Application Priority Data
May 8, 2017   (EP) .................................... 17275063

(51) Int. Cl.
| | |
|---|---|
| *A23L 29/10* | (2016.01) |
| *A21D 2/16* | (2006.01) |
| *A21D 13/80* | (2017.01) |
| *A23D 7/00* | (2006.01) |
| *A23D 7/01* | (2006.01) |
| *A23D 7/04* | (2006.01) |
| *A23G 3/40* | (2006.01) |
| *C09K 23/00* | (2022.01) |
| *C09K 23/34* | (2022.01) |
| *C12P 7/6445* | (2022.01) |

(52) U.S. Cl.
CPC ............ *C09K 23/018* (2022.01); *A21D 2/165* (2013.01); *A21D 13/80* (2017.01); *A23D 7/003* (2013.01); *A23D 7/011* (2013.01); *A23D 7/04* (2013.01); *A23G 3/40* (2013.01); *A23L 29/10* (2016.08); *C09K 23/34* (2022.01); *C12P 7/6445* (2013.01); *A23V 2002/00* (2013.01)

(58) Field of Classification Search
CPC ..... B01F 17/0092; A23L 29/10; A21D 13/80; A21D 2/165; A23D 7/003; A23D 7/011; A23D 7/04
See application file for complete search history.

(56) References Cited

U.S. PATENT DOCUMENTS

| | | | |
|---|---|---|---|
| 3,889,005 A | 6/1975 | Brammer et al. | |
| 2005/0214436 A1* | 9/2005 | Doucet | A21D 13/40 |
| | | | 426/606 |
| 2005/0233015 A1* | 10/2005 | Norberg | A61Q 19/00 |
| | | | 424/769 |
| 2009/0285876 A1* | 11/2009 | Hein | A61K 8/375 |
| | | | 424/443 |
| 2010/0112650 A1 | 5/2010 | Suzuki et al. | |
| 2011/0256264 A1 | 10/2011 | Soe | |
| 2015/0208686 A1* | 7/2015 | Piispa | A23D 9/02 |
| | | | 426/606 |
| 2016/0008262 A1 | 1/2016 | Hein et al. | |

FOREIGN PATENT DOCUMENTS

| | | | | |
|---|---|---|---|---|
| EP | 0547658 A1 | 6/1993 | | |
| EP | 2636313 A1 | 9/2013 | | |
| WO | 95/22256 A1 | 8/1995 | | |
| WO | WO-2008059220 A1 * | 5/2008 | ............. | A23D 7/011 |
| WO | 2014/020114 A1 | 2/2014 | | |
| WO | 2015/150405 A1 | 10/2015 | | |

OTHER PUBLICATIONS

International Search Report issued in corresponding International Patent Application No. PCT/EP2018/061613 dated Jun. 26, 2018.
International Preliminary Report on Patentability and Written Opinion issued in corresponding International Patent Application No. PCT/EP2018/061613 dated Nov. 12, 2019.
Yeoh et al., "Molecular distillation and characterization of diacylglycerol-enriched palm olein," European Journal of Lipid Science and Technology, 116: 1654-1663 (2014).
Hinrichsen, "Commercially available alternatives to palm oil," Lipid Technology, 28: 65-67 (2016).
Yeoh et al., "Influence of silica gel in production of diacylglycerol via enzymatic glycerolysis of palm olein," European Journal of Lipid Science and Technology, 111: 599-606 (2009).
Gunstone et al., The Lipid Handbook, Second Edition, 93, 101, 118-122 (1994).
K. Campbell-Timperman et al. "Mono- and Diglycerides Prepared by Chemical Glycerolysis from a Butterfat Fraction" Journal of Food Science, vol. 61, No. 1, (1996) pp. 44-47.
Codex Alimentarius "Standard for Named Vegetable Oils" World Health Organization, (1999), cxs 210-1999, pp. 2-15.

(Continued)

*Primary Examiner* — Stephanie A Cox
(74) *Attorney, Agent, or Firm* — Morgan, Lewis & Bockius LLP

(57) ABSTRACT

A non-hydrogenated, non-palm emulsifier composition comprises: at least 20% by weight monoglycerides; less than 60% by weight of diglycerides; and from 0-80% by weight triglycerides, wherein the weight % is with respect to the total of monoglycerides, diglycerides and triglycerides, and wherein the fatty acid residues bound to the monoglycerides, diglycerides and triglycerides in the emulsifier composition comprise: from 20% to 75% by weight stearic acid (C18:0); from 15% to 60% by weight oleic acid (C18:1); and from 1% to 10% by weight palmitic acid (C16:0), based on the total weight of C8 to C24 fatty acids. The composition is obtainable by a method comprising the reaction of a fat with glycerol in the presence of an enzymatic catalyst.

8 Claims, No Drawings

(56) References Cited

OTHER PUBLICATIONS

N. De Clercq "Changing the functionality of cocoa butter" PHD Thesis, Ghent University, (2011), Belgium, pp. 220.
R. Timms "Confectionery Fats Handbook" The Oily Press, PJ Barnes Associates, (2003), Bridgwater, England, pp. 176.
File history to U.S. Appl. No. 16/499,583.
Zielinski, Synthesis and Composition of Food-Grade Emulsifiers, G.L. Hasenhuettl (ed.), from Food Emulsifiers and Their Applications.

\* cited by examiner

EMULSIFIERS

This invention relates to an emulsifier composition, to the use of the composition as an emulsifier and to a method for preparing the composition.

Emulsifiers are used in many applications where it is desired to mix two generally immiscible phases, which are typically aqueous and non-aqueous. Emulsifiers find use in the food industry as well as in other applications such as cosmetics.

Compounds having a relatively polar moiety and a non-polar moiety may have emulsifying properties. Lecithin is an emulsifier that is commonly used in the food industry. Mono- and di-glycerides are also examples of emulsifiers. For example, monoglycerides are used as emulsifiers in the confectionery fillings described in EP-A-0547658.

WO 2014/020114 relates to a fat blend composition for a fat spread for lowering cholesterol levels. The fatty acid composition of the blend comprises 20% or less saturated fatty acids, of which 38% or less are palmitic acid and 20% or more are stearic acid.

WO 2015/150405 discloses a free fatty acid composition which comprises: greater than 60% by weight stearic acid; from 3 to 30% by weight oleic acid; and less than 10% by weight palmitic acid. The composition may be used in the preparation of a triglyceride.

US 2016/0008262 describes a composition comprising the product from a reaction of a natural butter or natural oil such as shea butter with glycerin in the presence of a basic catalyst. The reaction products retain the unsaponifiable portion of the natural butter or natural oil. The products are self-emulsifiable and are described as being useful in personal care, cosmetic, pharmaceutical, paper and textile applications.

There is a need for improved emulsifiers. In particular, there is a need for emulsifiers that can be readily produced from convenient sources and/or that can increase the stability of an emulsion against separation into its constituent phases.

According to the present invention, there is provided a non-hydrogenated, non-palm emulsifier composition comprising:
  at least 20% by weight monoglycerides,
  less than 60% by weight of diglycerides and
  and from 0-80% by weight triglycerides,
    wherein the weight % is with respect to the total of monoglycerides, diglycerides and triglycerides, and
  wherein the fatty acid residues bound to the monoglycerides, diglycerides and triglycerides in the emulsifier composition comprise:
    from 20% to 75% by weight stearic acid (C18:0);
    from 15% to 60% by weight oleic acid (C18:1); and
    from 1% to 10% by weight palmitic acid (C16:0),
    based on the total weight of C8 to C24 fatty acids,
and wherein the emulsifier composition is obtainable by a method comprising the reaction of a fat with glycerol in the presence of an enzymatic catalyst.

In another aspect, the invention provides the use of an emulsifier composition of the invention as an emulsifier in a food application, such as bakery or confectionery, preferably in puff pastry, cake, Danish rolls or water based fillings.

Yet another aspect of the invention is a method for preparing an emulsifier composition of the invention, comprising the steps of
  providing a fat comprising triglycerides, and
  reacting the fat with glycerol in a glycerolysis reaction using an enzymatic catalyst.

It has surprisingly been found that emulsifier compositions prepared using an enzymatic catalyst can provide emulsions having improved stability compared, for example, to emulsifier compositions prepared by chemical routes such as base treatment. Without wishing to be bound by theory, it is believed that this may be due to the fact the enzymatic process may exert greater control over the selectivity of the reaction.

The term "fatty acid", as used herein, refers to straight chain saturated or unsaturated (including mono- and poly-unsaturated) carboxylic acids having from 8 to 24 carbon atoms (C8 to C24). A fatty acid having n carbon atoms and x double bonds may be denoted Cn:x. For example, palmitic acid may be denoted C16:0 and oleic acid may be denoted C18:1. Percentages of fatty acids in compositions referred to herein include acyl groups in tri-, di- and mono-glycerides present in the glycerides as is customary terminology in the art and are based on the total weight of C8 to C24 fatty acids. The fatty acid profile (i.e., composition) may be determined, for example, by fatty acid methyl ester analysis (FAME) using gas chromatography according to ISO 12966-2 and ISO 12966-4.

The composition of the invention is non-hydrogenated. This means that the composition is not prepared from a fat that has been subjected to hydrogenation to convert unsaturated fatty acyl groups to saturated fatty acyl groups. The requirement for the fat to be non-hydrogenated means that the content of trans fatty acid residues in the composition is typically less than 1% by weight based on total C8 to C24 fatty acids present, more preferably not more than 0.5% by weight.

The term "fat" refers to glyceride fats and oils containing fatty acid acyl groups and does not imply any particular melting point. The term "oil" is used synonymously with "fat". Fats predominantly comprise triglycerides.

The emulsifier composition of the invention comprises at least stearic, oleic and palmitic acids as fatty acid residues and typically will also contain other fatty acids as fatty acid residues. Fatty acid residues other than stearic, oleic and palmitic are typically present in the composition at a level of less than 10% by weight, more preferably less than 8% by weight, such as less than 5% by weight, based on total C8 to C24 fatty acids present.

Preferably, in the emulsifier composition of the invention, the weight ratio of stearic acid to oleic acid residues is from 4:1 to 1:4, more preferably from 3:1 to 1:3, even more preferably from 2:1 to 1:2. It will again be appreciated that the fatty acid residues of the emulsifier composition of the invention refers to acyl groups that are present as acyl groups bonded in monoglycerides, diglycerides and/or triglycerides.

Preferably, the fatty acid residues are from at least one non-palm source selected from shea, sal, mango or combinations thereof. Thus, the emulsifier composition is preferably obtainable from shea, sal, mango and combinations thereof. The non-palm source may be a butter (as obtained naturally) or a fraction thereof, such as a stearin or olein fraction. Most preferred non-palm sources are shea olein, shea stearin and sal olein, with shea olein being particularly preferred. Other non-palm sources include mango butter, mango stearin and mango olein.

The term non-palm refers to fat or oil products that are not obtained from oil palm species, including, for example, the African oil palm *Elaeis guineensis*, the American oil palm *Elaeis oleifera* and the maripa palm *Attalea maripa*.

The enzymatic catalyst is preferably a lipase, more preferably a lipase from *Candida antarctica*, most preferably

*Candida antarctica* lipase B. The lipase may be immobilised. *Candida antarctica* lipase B immobilized on acrylic resin is available as Novozym 435.

The emulsifier composition preferably comprises from 20% to 95% by weight monoglycerides, more preferably from 23% to 95% monoglycerides. Additionally or alternatively, the emulsifier composition preferably comprises from 1% to 50% by weight diglycerides.

Therefore, a preferred emulsifier composition comprises:
from 23% to 95% by weight monoglycerides,
from 1 to 50% by weight of diglycerides and
and from 1 to 30% by weight triglycerides,
wherein the weight % is with respect to the total of monoglycerides, diglycerides and triglycerides.

Preferably, the weight ratio of monoglycerides to diglycerides is higher than 1:10, preferably higher than 1:4.

Preferably, the fatty acid residues bound to the monoglycerides, diglycerides and triglycerides in the emulsifier composition comprise from 1% to 12% by weight linoleic acid (C18:2), more preferably from 1 to 10% linoleic acid.

The fatty acid residues bound to the monoglycerides, diglycerides and triglycerides in the emulsifier composition preferably comprise from 25% to 70% by weight stearic acid. Additionally or alternatively, the fatty acid residues bound to the monoglycerides, diglycerides and triglycerides in the emulsifier composition preferably comprise from 20% to 55% by weight oleic acid.

Preferably, the fatty acid residues bound to the monoglycerides, diglycerides and triglycerides in the emulsifier composition comprise from 1% to 8% by weight palmitic acid.

Thus, in a particularly preferred composition of the invention, the fatty acid residues bound to the monoglycerides, diglycerides and triglycerides comprise:
from 25% to 70% by weight stearic acid (C18:0);
from 20% to 55% by weight oleic acid (C18:1);
from 1 to 10% linoleic acid, and
from 1% to 8% by weight palmitic acid (C16:0),
based on the total weight of C8 to C24 fatty acids.

The emulsifier composition is obtainable, and is preferably obtained, by a method comprising the reaction of a fat with glycerol in the presence of an enzymatic catalyst. The method is preferably a method of the invention. In the reaction of the fat with glycerol, at least some of the triglycerides in the fat are converted to monoglycerides and diglycerides. The fat that is reacted with glycerol is preferably shea, sal or combinations thereof, or fractions thereof, more preferably shea olein, shea stearin or sal olein, with shea olein being particularly preferred.

The method of the invention for preparing an emulsifier composition of the invention comprises the steps of providing a fat comprising triglycerides, and reacting the fat with glycerol in a glycerolysis reaction using an enzymatic catalyst.

As described above in relation to the emulsifier composition of the invention, the enzymatic catalyst is a lipase, more preferably a lipase from *Candida antarctica*, most preferably *Candida antarctica* lipase B. The lipase may be immobilised.

In the method of the invention, the fat is preferably selected from shea butter, shea olein, shea stearin, sal butter, sal stearin, sal olein, and mixtures thereof. More preferably, the fat is shea olein, shea stearin or sal olein, most preferably shea olein.

The conditions for reacting the fat with glycerol and for the method of the invention preferably comprise reacting the fat with glycerol at a weight ratio of fat to glycerol in the range of from 10:1 to 2:1, more preferably from 5:1 to 3:1.

The reaction is carried out typically for 10 to 48 hours at a suitable temperature for the enzyme, preferably in the range of 55° C. to 70° C.

The method of the invention may comprise the further steps of bleaching and deodorization after the reaction of the fat with glycerol. Preferably, deodorization is carried out at a reduced pressure in the range of 0.5 mbar to 2 mbar at a temperature in the range of from 130° C. to 170° C.

In one embodiment, the method does not comprise a further purification step of distillation. The emulsifier composition produced by this method typically comprises:
20% to 30% by weight monoglycerides,
40% to 50% by weight of diglycerides and
15% to 30% by weight triglycerides,
wherein the weight % is with respect to the total of monoglycerides, diglycerides and triglycerides, and
wherein the fatty acid residues bound to the monoglycerides, diglycerides and triglycerides in the emulsifier composition preferably comprise:
from 20% to 40% by weight stearic acid (C18:0);
from 40% to 60% by weight oleic acid (C18:1); and
from 1% to 10% by weight palmitic acid (C16:0),
based on the total weight of C8 to C24 fatty acids.

The method of the invention, in another embodiment, comprises a step of distilling the product to enrich the emulsifier composition in monoglycerides. In this embodiment, the emulsifier composition produced by the method typically comprises:
80% to 95% by weight monoglycerides,
1% to 10% by weight of diglycerides and
and from 0.5% to 5% by weight triglycerides,
wherein the weight % is with respect to the total of monoglycerides, diglycerides and triglycerides, and
wherein the fatty acid residues bound to the monoglycerides, diglycerides and triglycerides in the emulsifier composition preferably comprise:
from 50% to 75% by weight stearic acid (C18:0);
from 15% to 35% by weight oleic acid (C18:1); and
from 1% to 10% by weight palmitic acid (C16:0),
based on the total weight of C8 to C24 fatty acids.

The invention also provides the use of an emulsifier composition of the invention as an emulsifier in a food application, such as bakery or confectionery. The use of the emulsifier may be for increasing the stability of an emulsion, such as a water-in-oil emulsion.

Emulsifier compositions of the invention may therefore be used in food applications. Examples of food applications are bakery or confectionery, preferably puff pastry, cake, Danish rolls or water based fillings.

Emulsifier compositions of the invention may, for example, be used in the production of bakery products. The bakery products may have a laminated structure. For bakery applications, the emulsifier composition is typically used in conjunction with a fat.

Margarine, bakery fat or puff pastry (i.e., laminating) fat and an emulsifier composition of the invention may be combined with flour and water to form a dough. The dough preferably comprises flour in an amount of from 30 to 60% by weight, water in an amount of from 10 to 40% by weight, the margarine, bakery fat or puff pastry (i.e., laminating) fat in an amount of from 10 to 50% by weight and from 0.04% to 0.75% by weight of an emulsifier composition of the invention based on the weight of the dough. Optionally, one or more further ingredients such as salt and flour modifier may be included in the dough. Bakery products are made from dough. The dough preferably has a laminated structure.

The bakery products include, for example, puff pastry, croissants, Danish pastries and pies.

Doughs comprising the emulsifier compositions, and a margarine, laminating fat and/or a bakery fat, may be refrigerated, frozen or otherwise stored prior to use. The frozen dough may be packaged and sold to the consumer. In order to form a bakery product, the dough is baked, preferably in an oven. Suitable times and temperatures for baking specific bakery products will be well-known to those skilled in the art.

Cake may be made from a batter that is baked. Cake batters typically comprise, in addition to the emulsifier composition, fat, sugar, flour, milk and eggs. The amount of emulsifier in the batter is typically in the range of 0.6% to 5.6% by weight.

A confectionery filling that is water based may comprise a fat-continuous emulsion with a fat content of 5-50 wt. % while the water content of the remainder is 10-60 wt. %, and the remainder further consists of 90-40 wt. % of at least one of the following components: acidity regulator, thickener, bulking agent, sweetener, flavour, colourant, humectant and preservative, together with the emulsifier. The emulsifier composition of the invention is typically present in an amount of from 0.08% to 1% by weight. The filling will preferably be used in encapsulated form when applied in confectionery products. By the expression "encapsulated" is meant that the filling is surrounded by a coating layer or shell, preferably consisting of, or containing, chocolate. In these cases, the shell, in particular the chocolate shell, represents 20-50 wt % of the total product.

The listing or discussion of an apparently prior-published document in this specification should not necessarily be taken as an acknowledgement that the document is part of the state of the art or is common general knowledge.

Preferences and options for a given aspect, embodiment, feature or parameter of the invention should, unless the context indicates otherwise, be regarded as having been disclosed in combination with any and all preferences and options for all other aspects, embodiments, features and parameters of the invention. In particular, it will be appreciated that features of the method of the invention apply to the emulsifier composition of the invention and vice versa.

The following non-limiting examples illustrate the invention and do not limit its scope in any way. In the examples and throughout this specification, all percentages, parts and ratios are by weight unless indicated otherwise.

EXAMPLES

Example 1

Crude shea olein is obtained after solvent fractionation of crude shea butter. The fatty acid composition of the products in w/w is given in the following Table 1.

| | |
|---|---|
| C8:0 | 0 |
| C10:0 | 0 |
| C12:0 | 0 |
| C15:0 | 0 |
| C14:0 | 0.1 |
| C16:0 | 5.1 |
| C16:1C | 0.1 |
| C16:1T | 0 |
| C17:0 | 0.1 |
| C18:0 | 31.9 |
| C18:1 | 52.3 |
| C18:1T | 0 |
| C18:1C | 52.2 |
| C18:2 | 8 |
| C18:2T | 0 |
| C18:2C | 8 |
| C18:3 | 0.3 |
| C18:3T | 0.1 |
| C18:3C | 0.2 |
| Total Trans | 0.1 |
| C20:0 | 1.2 |
| C20:1C | 0.4 |
| C20:2C | 0 |
| C22:0 | 0.1 |
| C22:1 | 0 |
| C22:1T | 0 |
| C22:1C | 0 |
| C24:0 | 0.1 |
| C24:1C | 0 |

In the above table:
Cx:y refers to a fatty acid having x carbon atoms and y double bonds;
C refers to cis fatty acids and T to trans fatty acids; levels determined by GC-FAME (ISO 12966-2 and ISO 12966-4).

400 g of the crude shea olein was esterified with 102.4 g glycerol in the presence of immobilized lipase originating from *Candida antarctica* B (Novozym® 435). When the reaction was completed, after approximatively 24 hours, the product was filtered. Then this product was bleached and deodorised at low temperature (mild refining) to obtain the emulsifier composition, which has the following composition, w/w (Table 2):

| | |
|---|---|
| C8:0 | 0 |
| C10:0 | 0 |
| C12:0 | 0 |
| C15:0 | 0 |
| C14:0 | 0.1 |
| C16:0 | 4.9 |
| C16:1C | 0.1 |
| C16:1T | 0 |
| C17:0 | 0.1 |
| C18:0 | 32.5 |
| C18:1 | 52.2 |
| C18:1T | 0 |
| C18:1C | 52.2 |
| C18:2 | 7.9 |
| C18:2T | 0 |
| C18:2C | 7.9 |
| C18:3 | 0.3 |
| C18:3T | 0.1 |
| C18:3C | 0.2 |
| Total Trans | 0.2 |
| C20:0 | 1.3 |
| C20:1C | 0.4 |
| C20:2C | 0 |
| C22:0 | 0.1 |
| C22:1 | 0 |
| C22:1T | 0 |
| C22:1C | 0 |
| C24:0 | 0.1 |
| C24:1C | 0 |
| Triglyceride | 21.9 |
| Diglyceride | 43.4 |
| Monoglyceride | 23.8 |

In the above table:
Cx:y refers to a fatty acid having x carbon atoms and y double bonds;
C refers to cis fatty acids and T to trans fatty acids; levels determined by GC-FAME (ISO 12966-2 and ISO 12966-4); Triglyceride/Diglyceride/Monoglyceride determined by HPLC (ISO 18395: 2005(E)).

Example 2

600 g refined shea stearin obtained from shea butter by solvent fractionation was esterified with 76.8 g glycerol in the presence of immobilized lipase originating from *Candida antarctica* B (Novozym® 435). When the reaction was completed, after approximatively 24 hours, the product was filtered. The product has the following composition, w/w (Table 3):

| | |
|---|---|
| C8:0 | 0 |
| C10:0 | 0 |
| C12:0 | 0.1 |
| C15:0 | 0 |
| C14:0 | 0.1 |
| C16:0 | 3.6 |
| C16:1C | 0 |
| C16:1T | 0 |
| C17:0 | 0.1 |
| C18:0 | 59.7 |
| C18:1 | 31.5 |
| C18:1T | 0 |
| C18:1C | 31.4 |
| C18:2 | 2.9 |
| C18:2T | 0.1 |
| C18:2C | 2.8 |
| C18:3 | 0.1 |
| C18:3T | 0 |
| C18:3C | 0.1 |
| Total Trans | 0.1 |
| C20:0 | 1.7 |
| C20:1C | 0 |
| C20:2C | 0 |
| C22:0 | 0.2 |
| C22:1 | 0 |
| C22:1T | 0 |
| C22:1C | 0 |
| C24:0 | 0.1 |
| C24:1C | 0 |
| Triglyceride | 26.3 |
| Diglyceride | 45.5 |
| Monoglyceride | 26.8 |

In the above table:
Cx:y refers to a fatty acid having x carbon atoms and y double bonds;
C refers to cis fatty acids and T to trans fatty acids; levels determined by GC-FAME (ISO 12966-2 and ISO 12966-4);
Triglyceride/Diglyceride/Monoglyceride determined by HPLC (ISO 18395: 2005(E)).

The product containing monoglycerides was distilled in order to separate monoglycerides from triglycerides and diglycerides by means of short path distillation at a temperature of about 180° C. and a pressure of about $1 \times 10^{-2}$ mbar. The concentrated monoglyceride product was collected as distillate. The concentrated monoglyceride emulsifier composition has the following composition, w/w (Table 4):

| | |
|---|---|
| C8:0 | 0 |
| C10:0 | 0 |
| C12:0 | 0.2 |
| C15:0 | 0 |
| C14:0 | 0.1 |
| C16:0 | 5.5 |
| C16:1C | 0 |
| C16:1T | 0 |
| C17:0 | 0.1 |
| C18:0 | 66.2 |
| C18:1 | 24 |
| C18:1T | 0 |
| C18:1C | 23.9 |
| C18:2 | 2.2 |
| C18:2T | 0 |
| C18:2C | 2.2 |
| C18:3 | 0 |
| C18:3T | 0 |
| C18:3C | 0 |
| Total Trans | 0 |
| C20:0 | 1.5 |
| C20:1C | 0 |
| C20:2C | 0 |
| C22:0 | 0.1 |
| C22:1 | 0 |
| C22:1T | 0 |
| C22:1C | 0 |
| C24:0 | 0 |
| C24:1C | 0 |
| Triglyceride | 1.2 |
| Diglyceride | 5.7 |
| Monoglyceride | 91.3 |

In the above table:
Cx:y refers to a fatty acid having x carbon atoms and y double bonds;
C refers to cis fatty acids and T to trans fatty acids; levels determined by GC-FAME (ISO 12966-2 and ISO 12966-4);
Triglyceride/Diglyceride/Monoglyceride determined by HPLC (ISO 18395: 2005(E))

Example 3

Sal olein is obtained after solvent fractionation of sal butter. The fatty acid composition of the product is given in the following Table 5.

| | |
|---|---|
| C8:0 | 0 |
| C10:0 | 0 |
| C12:0 | 0 |
| C15:0 | 0.1 |
| C14:0 | 0.1 |
| C16:0 | 7.5 |
| C16:1C | 0.1 |
| C16:1T | 0 |
| C17:0 | 0.2 |
| C18:0 | 28.2 |
| C18:1 | 53.2 |
| C18:1T | 0.4 |
| C18:1C | 52.8 |
| C18:2 | 3.4 |
| C18:2T | 0 |
| C18:2C | 3.4 |
| C18:3 | 0.9 |
| C18:3T | 0.1 |
| C18:3C | 0.8 |
| Total Trans | 0.5 |
| C20:0 | 4.7 |
| C20:1C | 0.6 |
| C20:2C | 0.1 |
| C22:0 | 0.4 |
| C22:1 | 0 |
| C22:1T | 0 |
| C22:1C | 0 |
| C24:0 | 0.2 |
| C24:1C | 0 |

In the above table:
Cx:y refers to a fatty acid having x carbon atoms and y double bonds;
C refers to cis fatty acids and T to trans fatty acids; levels determined by GC-FAME (ISO 12966-2 and ISO 12966-4).

420 g sal olein was esterified with 105 g glycerol in the presence of immobilized lipase originating from *Candida antarctica* B (Novozym® 435). When the reaction was completed, after approximatively 24 hours, the product was filtered. Then this product was bleached and deodorised at low temperature (mild refining) to obtain the emulsifier composition, which has the following composition, w/w (Table 6):

| | |
|---|---|
| C8:0 | 0 |
| C10:0 | 0 |
| C12:0 | 0 |
| C15:0 | 0.1 |
| C14:0 | 0.1 |
| C16:0 | 7.4 |
| C16:1C | 0.1 |
| C16:1T | 0 |
| C17:0 | 0.2 |
| C18:0 | 28.3 |
| C18:1 | 53.2 |
| C18:1T | 0.4 |
| C18:1C | 52.8 |
| C18:2 | 3.4 |
| C18:2T | 0 |
| C18:2C | 3.4 |
| C18:3 | 0.9 |
| C18:3T | 0.1 |
| C18:3C | 0.8 |
| Total Trans | 0.5 |
| C20:0 | 4.8 |
| C20:1C | 0.6 |
| C20:2C | 0.1 |
| C22:0 | 0.4 |
| C22:1 | 0 |
| C22:1T | 0 |
| C22:1C | 0 |
| C24:0 | 0.2 |
| C24:1C | 0 |
| Triglyceride | 24 |
| Diglyceride | 47.8 |
| Monoglyceride | 24.7 |

In the above table:
Cx:y refers to a fatty acid having x carbon atoms and y double bonds;
C refers to cis fatty acids and T to trans fatty acids; levels determined by GC-FAME (ISO 12966-2 and ISO 12966-4); Triglyceride/Diglyceride/Monoglyceride determined by HPLC (ISO 18395: 2005(E)).

Comparative Example 271.7 g refined shea butter was reacted with 26.9 g glycerol in the presence of 1.5 g potassium hydroxide flakes at 200° C. and under vacuum lower than 100 mbar. When the reaction was completed, after approximatively 30 minutes, the product was bleached and deodorized in order to obtain a comparative example, which has the following composition (Table 7):

| | |
|---|---|
| C8:0 | 0 |
| C10:0 | 0 |
| C12:0 | 0.4 |
| C15:0 | 0 |
| C14:0 | 0.2 |
| C16:0 | 4 |
| C16:1C | 0.1 |
| C16:1T | 0 |
| C17:0 | 0.1 |
| C18:0 | 43.9 |
| C18:1 | 43.3 |
| C18:1T | 0.1 |
| C18:1C | 43.2 |
| C18:2 | 5.8 |
| C18:2T | 0.1 |
| C18:2C | 5.8 |
| C18:3 | 0.2 |
| C18:3T | 0.1 |
| C18:3C | 0.1 |
| Total Trans | 0.2 |
| C20:0 | 1.4 |
| C20:1C | 0.2 |
| C20:2C | 0 |
| C22:0 | 0.1 |
| C22:1 | 0 |
| C22:1T | 0 |
| C22:1C | 0 |
| C24:0 | 0.1 |
| C24:1C | 0 |
| Triglyceride | 10.7 |
| Diglyceride | 48.3 |
| Monoglyceride | 40.2 |

In the above table:
Cx:y refers to a fatty acid having x carbon atoms and y double bonds;
C refers to cis fatty acids and T to trans fatty acids; levels determined by GC-FAME (ISO 12966-2 and ISO 12966-4); Triglyceride/Diglyceride/Monoglyceride determined by HPLC (ISO 18395: 2005(E))

Example 4

An emulsion stability test was performed in order to evaluate the functionality of emulsifiers. Besides the comparative example, a commercial emulsifier product Durem 35NG from IOI Loders Crokaan US was also included, which has the following composition (Table 8):

| | |
|---|---|
| C8:0 | 0 |
| C10:0 | 0 |
| C12:0 | 0.3 |
| C15:0 | 0.1 |
| C14:0 | 1.1 |
| C16:0 | 42.3 |
| C16:1C | 0.2 |
| C16:1T | 0 |
| C17:0 | 0.1 |
| C18:0 | 4.6 |
| C18:1 | 41.1 |
| C18:1T | 0.1 |
| C18:1C | 41 |
| C18:2 | 9.2 |
| C18:2T | 0.6 |
| C18:2C | 8.6 |
| C18:3 | 0.2 |
| C18:3T | 0.1 |
| C18:3C | 0.1 |
| Total Trans | 0.8 |
| C20:0 | 0.4 |
| C20:1C | 0.2 |
| C20:2C | 0 |
| C22:0 | 0.1 |
| C22:1 | 0 |
| C22:1T | 0 |
| C22:1C | 0 |
| C24:0 | 0.1 |
| C24:1C | 0 |
| Triglyceride | 10.7 |
| Diglyceride | 48.3 |
| Monoglyceride | 40.2 |

In the above table:
Cx:y refers to a fatty acid having x carbon atoms and y double bonds;
C refers to cis fatty acids and T to trans fatty acids; levels determined by GC-FAME (ISO 12966-2 and ISO 12966-4); Triglyceride/Diglyceride/Monoglyceride determined by HPLC (ISO 18395: 2005(E)).

0.8 g emulsifier of Example 1, Example 3, Comparative example and Durem 35NG was totally dissolved in 80 g rapeseed oil respectively. Each mixture was put into a 120 ml glass bottle and mixed with a propeller with four symmetrical square blades of 0.8 cm each at a speed of 750 rpm. When the temperature of each mixture is at approximatively 30° C., 20 ml demineralized water was gently added into each mixture within 15 seconds. Each emulsion was further mixed at room temperature under the same mixing conditions for 1 minute. Then, each emulsion was poured into a 100 ml glass graduated cylinder at room temperature. After 30 min, the volume of water layer was read respectively in order to evaluate the emulsion stability. One control test was done without any emulsifier. The stability was calculated with the following formula:

$$\text{Emulsion stability \%} = \frac{20 - \text{Volume of water layer after separation}}{20} \%$$

The results are shown in the following table (Table 9):

|  | Control | Example 1 | Example 3 | Comparative example | Durem 35NG |
|---|---|---|---|---|---|
| Volume of water layer after separation (ml) | 17 | 10 | 12 | 15 | 13 |
| Emulsion stability % | 15% | 50% | 40% | 25% | 35% |

Example 1 and Example 3 show better emulsion stability than the Comparative example and Durem 35NG.

Example 5

An emulsion stability test was performed in order to evaluate the functionality of the emulsifiers. A commercial emulsifier product Dimodan HP MB from Danisco, DuPont Group was included, which has the following composition (Table 10):

| | |
|---|---|
| C8:0 | 0 |
| C10:0 | 0 |
| C12:0 | 0.3 |
| C15:0 | 0.1 |
| C14:0 | 1.2 |
| C16:0 | 55.2 |
| C16:1C | 0 |
| C16:1T | 0 |
| C17:0 | 0.1 |
| C18:0 | 42.4 |
| C18:1 | 0.1 |
| C18:1T | 0 |
| C18:1C | 0 |
| C18:2 | 0 |
| C18:2T | 0 |
| C18:2C | 0 |
| C18:3 | 0 |
| C18:3T | 0 |
| C18:3C | 0 |
| Total Trans | 0 |
| C20:0 | 0.5 |
| C20:1C | 0 |
| C20:2C | 0 |
| C22:0 | 0.1 |
| C22:1 | 0 |
| C22:1T | 0 |
| C22:1C | 0 |
| C24:0 | 0.1 |
| C24:1C | 0 |

-continued

| | |
|---|---|
| Triglyceride | 0.1 |
| Diglyceride | 2.5 |
| Monoglyceride | 97.1 |

0.4 g emulsifier of either Example 2 or Dimodan HP MB were totally dissolved in 80 g rapeseed oil respectively. Each mixture was put into a 120 ml glass bottle and mixed with a propeller with four symmetrical square blades of 0.8 cm each at a speed of 750 rpm. When the temperature of each mixture is at approximatively 30° C., 20 ml demineralized water was gently added into each mixture within 15 seconds. Each emulsion was further mixed at room temperature under the same mixing conditions for 1 minute. Then, each emulsion was poured into a 100 ml glass graduated cylinder at room temperature. After 30 min, the volume of water layer was read respectively in order to evaluate the emulsion stability. One control test was done without any emulsifier. The stability was calculated with the following formula:

$$\text{Emulsion stability \%} = \frac{20 - \text{Volume of water layer after separation}}{20} \%$$

The results are shown in the following table (Table 11):

|  | Control | Example 2 | Dimodan HP MB |
|---|---|---|---|
| Volume of water layer after separation (ml) | 17 | 13 | 15 |
| Emulsion stability % | 15% | 35% | 25% |

Example 2 shows better emulsion stability than Dimodan HP MB.

The invention claimed is:

1. A non-hydrogenated, non-palm emulsifier composition comprising:
   20% to 30% by weight monoglycerides;
   40% to 50% by weight of diglycerides; and
   from 15% to 30% by weight triglycerides,
   wherein the weight % is with respect to the total of the monoglycerides, diglycerides and triglycerides, and
   wherein fatty acid residues bound to the monoglycerides, diglycerides and triglycerides in the emulsifier composition comprise:
   from 20% to 40% by weight stearic acid (C18:0);
   from 40% to 60% by weight oleic acid (C18:1); and
   from 1% to 10% by weight palmitic acid (C16:0),
   based on the total weight of C8 to C24 fatty acids,
   and wherein the composition is obtained by a method comprising the reaction of a fat with glycerol in the presence of an enzymatic catalyst,
   and the fat is from at least one non-palm source, wherein the non-palm source comprises shea olein, sal olein or combinations thereof.

2. The composition according to claim 1, wherein the enzymatic catalyst is a lipase.

3. The composition according to claim 1, comprising from 1% to 12% by weight linoleic acid (C18:2).

4. The composition according to claim 1, comprising from 1% to 10% by weight linoleic acid (C18:2).

5. The composition according to claim 1, comprising from 1% to 8% by weight palmitic acid.

6. A food product comprising the composition according to claim 1.

7. The food product according to claim 6, wherein the food product is selected from the group consisting of puff pastry, cake, Danish rolls and water-based fillings.

8. A method for preparing the emulsifier composition according to claim 1, comprising:
   providing a fat comprising triglycerides wherein the fat is selected from shea olein, sal olein, and mixtures thereof, and
   reacting the fat with glycerol in a glycerolysis reaction in the presence of an enzymatic catalyst.

* * * * *